United States Patent
Kida et al.

(10) Patent No.: US 6,421,126 B1
(45) Date of Patent: Jul. 16, 2002

(54) DENSITY CHECKING APPARATUS FOR TOBACCO FLAVOR-TASTING ARTICLE OR COMPONENT OF TOBACCO FLAVOR-TASTING ARTICLE

(75) Inventors: Shinzo Kida; Yoshiaki Ishikawa, both of Tokyo (JP)

(73) Assignee: Japan Tobacco Inc., Tokyo (JP)

( * ) Notice: Subject to any disclaimer, the term of this patent is extended or adjusted under 35 U.S.C. 154(b) by 0 days.

(21) Appl. No.: 09/988,770

(22) Filed: Nov. 20, 2001

Related U.S. Application Data

(63) Continuation of application No. PCT/JP00/07455, filed on Oct. 25, 2000.

(51) Int. Cl.$^7$ .......................... G01N 21/00; A24C 5/14
(52) U.S. Cl. .................. 356/432; 356/237.1; 131/905; 131/906; 131/908
(58) Field of Search .............................. 356/432, 433, 356/434, 435, 436, 437, 438, 439, 440, 237.1, 237.2, 445–448; 131/280, 84.1, 905, 906, 908; 209/536, 939; 250/252.1, 223 R, 358, 359.1; 378/54

(56) References Cited

U.S. PATENT DOCUMENTS

| | | | |
|---|---|---|---|
| 4,424,443 A | 1/1984 | Reuland | |
| 4,805,641 A | * 2/1989 | Radzio et al. | 131/280 |
| 4,865,054 A | 9/1989 | Lorenzen et al. | |
| 4,986,285 A | * 1/1991 | Radzio et al. | 131/280 |
| 5,335,229 A | 8/1994 | Hunt et al. | |
| 5,651,041 A | * 7/1997 | Moller et al. | 131/905 |

FOREIGN PATENT DOCUMENTS

| JP | A57-69216 | 4/1982 |
|---|---|---|
| JP | A2000-3339663 | 5/2000 |

* cited by examiner

Primary Examiner—Hoa Q. Pham
(74) Attorney, Agent, or Firm—Birch, Stewart, Kolasch & Birch, LLP

(57) ABSTRACT

In an optical density checking apparatus, a 0.7-$\mu$m first light beam not transmitted through shredded leaf tobacco and a 1.3-$\mu$m second light beam transmitted through the shredded leaf tobacco, which are from first and second light sources, are synthesized, and an obtained synthetic light beam is applied to a tobacco rod. The projected light quantities, reflected light quantities, and passing light quantities of the first and second light beams are measured by a composite light-receiving element, projected light quantity control circuit, and arithmetic circuit. The arithmetic circuit calculates the transmitted light quantity of the second light beam transmitted through the shredded leaf tobacco on the basis of the projected light quantities, reflected light quantities, and passing light quantities of the first and second light beams, and calculates the density of the shredded leaf tobacco on the basis of the transmitted light quantity.

12 Claims, 3 Drawing Sheets

DENSITY CHECKING APPARATUS FOR TOBACCO FLAVOR-TASTING ARTICLE OR COMPONENT OF TOBACCO FLAVOR-TASTING ARTICLE

CROSS REFERENCE TO RELATED APPLICATIONS

This is a Continuation Application of PCT Application No. PCT/JP00/07455, filed Oct. 25, 2000, which was not published under PCT Article 21(2) in English.

BACKGROUND OF THE INVENTION

1. Field of the Invention

The present invention relates to a checking apparatus directed to as a test target a rod-like flavor-tasting article or a component thereof having an aggregate of a large number of small pieces, such as shredded leaf tobacco, to optically check the density of the small pieces. This checking apparatus can be used in, e.g., a system that manufactures a tobacco rod by wrapping shredded leaf tobacco with a wrapper, to feedback-control the amount of shredded leaf tobacco introduced to the tobacco rod and to eliminate a defective tobacco rod.

2. Description of the Related Art

In a process of manufacturing a flavor-tasting article such as a cigarette, tobacco rod, or tobacco filter, or a component of the same, to know whether the product is defective or not, the density of each constituent member of the flavor-tasting article must be checked. For example, in a system for manufacturing a tobacco rod by wrapping shredded leaf tobacco with a wrapper, an optical density checking apparatus is used to obtain the packed state of the shredded leaf tobacco in the tobacco rod. As a checking apparatus of this type, Jpn. Pat. Appln. KOKOKU Publication No. 8-2288 (corresponding to U.S. Pat. Nos. 4,805,641 and 4,986,285) discloses an apparatus for optically checking the density of a tobacco strand by using a light beam within a range of ultraviolet rays to infrared rays.

The present inventor checked the density of a tobacco rod by using a checking apparatus of the type disclosed in the above reference. The correlation between the light attenuation ratio and the weight of the shredded leaf tobacco was not accurately obtained depending on the characteristics of the shredded leaf tobacco in the tobacco rod. This problem may be posed because the following several important factors are not sufficiently considered.

First, the water contained in the shredded leaf tobacco largely influences the correlation between the light attenuation ratio and the weight of the shredded leaf tobacco. When the light-emitting element is an LED, the emitted light is not a single-wavelength light, but its wavelength band is wide, and accordingly the ratio of light attenuation caused by the shredded leaf tobacco changes depending on the wavelength. Because light is transmitted through the clearance of the packed shredded leaf tobacco or along the surface of the wrapper of the rod (which is influenced by circumferential change of the tobacco rod), the quantity of light coming incident on the light-receiving element is larger than that calculated considering the quantity of light actually attenuated by the shredded leaf tobacco. Furthermore, a measurement error occurs due to the dark current of the light-receiving element.

BRIEF SUMMARY OF THE INVENTION

The present invention has been made in view of the problems of the prior art described above, and has as its object to provide a density checking apparatus which is directed to as a test target a rod-like flavor-tasting article or a component thereof having an aggregate of a large number of small pieces, such as shredded leaf tobacco, and which can optically check the density of the small pieces at high precision.

According to the first aspect of the present invention, there is provided an apparatus directed to as a test target a rod-like flavor-tasting article or a component thereof having an aggregate of a large number of small pieces, to optically check the density of the small pieces, comprising:

a first light source configured to emit a first light beam formed of light with a first wavelength not substantially transmitted through the small pieces;

a second light source configured to emit a second light beam formed of light with a second wavelength substantially transmitted through the small piece;

an optical system configured to synthesize the first and second light beams and to irradiate the test target with an obtained synthetic light beam;

a first measurement unit configured to measure first and second projected light quantities respectively corresponding to the first and second light beams included in the synthetic light beam before applied to the test target;

a second measurement unit configured to measure first and second reflected light quantities respectively corresponding to the first and second light beams included in the synthetic light beam reflected by a surface of the test target;

a third measurement unit configured to measure first and second passing light quantities respectively corresponding to the first and second light beams included in the synthetic light beam passing through the test target; and an arithmetic circuit configured to calculate a transmitted light quantity of the second light beam transmitted through the small pieces on the basis of the first and second projected light quantities, first and second reflected light quantities, and first and second passing light quantities, and to calculate the density of the small pieces on the basis of the transmitted light quantity.

According to the second aspect of the present invention, in the apparatus according to the first aspect, the second measurement unit measures the first and second reflected light quantities by receiving and detecting both the first and second light beams included in the synthetic light beam reflected by the surface of the test target.

According to the third aspect of the present invention, in the apparatus according to the first aspect, the second measurement unit measures one of the first and second reflected light quantities by receiving and detecting one of the first and second light beams included in the synthetic light beam reflected by the surface of the test target, and measures the other one of the first and second reflected light quantities by calculation with a premise that the other one of the first and second reflected light quantities can be obtained with the same reflectance as that of one of the reflected light quantities.

According to the fourth aspect of the present invention, the apparatus according to any one of the first to third aspects further comprises a detection circuit configured to calculate a fluctuation value as a difference between a reference value representing the density of the small pieces and a measurement value of the density of the small pieces which is obtained by the arithmetic circuit, and a control circuit configured to control an amount of the small pieces to be introduced into the test target in a manufacturing system for the test target on the basis of the fluctuation value.

According to the fifth aspect of the present invention, the apparatus according to the fourth aspect further comprises an integrating circuit configured to calculate an average value of fluctuation values of a plurality of test targets obtained with the detection circuit and to transmit the average value to the control circuit.

According to the sixth aspect of the present invention, the apparatus according to the fourth or fifth aspect further comprises a comparative determination circuit configured to compare the fluctuation value and a threshold value and to determine whether the test target is defective or not.

According to the seventh aspect of the present invention, in the apparatus according to any one of the first to sixth aspects, the small pieces are shredded leaf tobacco, and the first and second wavelengths are 0.5 $\mu$m to 0.8 $\mu$m and 1.2 $\mu$m to 1.4 $\mu$m, respectively.

According to the eighth aspect of the present invention, in the apparatus according to any one of the first to seventh aspects, each of the first and second light beams comprises a laser light beam.

According to the ninth aspect of the present invention, in the apparatus according to the eighth aspect, at least one of the first to third measurement units has a composite light-receiving element configured to receive and detect the first and second light beams on one optical path.

According to the 10th aspect of the present invention, in the apparatus according to any one of the first to ninth aspects, the synthetic light beam applied from the optical system to the test target comprises a parallel light beam.

According to the 11th aspect of the present invention, in the apparatus according to any one of the first to 10th aspects, the first measurement unit measures the first and second projected light quantities by receiving and detecting the first and second light beams included in a beam portion separated from the synthetic light beam between the optical system and the test target.

According to the 12th aspect of the present invention, the apparatus according to any one of the first to 11th aspect further comprises a mirror, which is disposed between the optical system and the test target, and has a mirror surface facing the test target to be inclined with respect thereto and a hole matching with an optical axis of the optical system, wherein the synthetic light beam from the optical system passes through the hole as a convergent light beam with a focal point falling on the hole and is thereafter applied to the test target, and the synthetic light beam reflected by the surface of the test target is reflected by the mirror and is introduced to the second measurement unit.

The embodiments of the present invention include inventions at various stages, and various types of inventions can be extracted from appropriate combinations of a plurality of disclosed constituent elements. For example, when an invention is extracted by omitting several ones from all constituent elements shown in the embodiments, to practice the extracted invention, the omitted portions are compensated for by known conventional technique.

According to the present invention, in an optical density checking apparatus directed to as a test target a rod-like flavor-tasting article or a component thereof having an aggregate of a large number of small pieces, such as shredded leaf tobacco, when the first light beam not substantially transmitted through the small pieces and the second light beam substantially transmitted through the small pieces are used, the density of the small pieces can be checked at high precision.

Additional objects and advantages of the invention will be set forth in the description which follows, and in part will be obvious from the description, or may be learned by practice of the invention. The objects and advantages of the invention may be realized and obtained by means of the instrumentalities and combinations particularly pointed out hereinafter.

BRIEF DESCRIPTION OF THE SEVERAL VIEWS OF THE DRAWING

The accompanying drawings, which are incorporated in and constitute a part of the specification, illustrate embodiments of the invention, and together with the general description given above and the detailed description of the embodiments given below, serve to explain the principles of the invention.

DETAILED DESCRIPTION OF THE INVENTION

Figure 1:
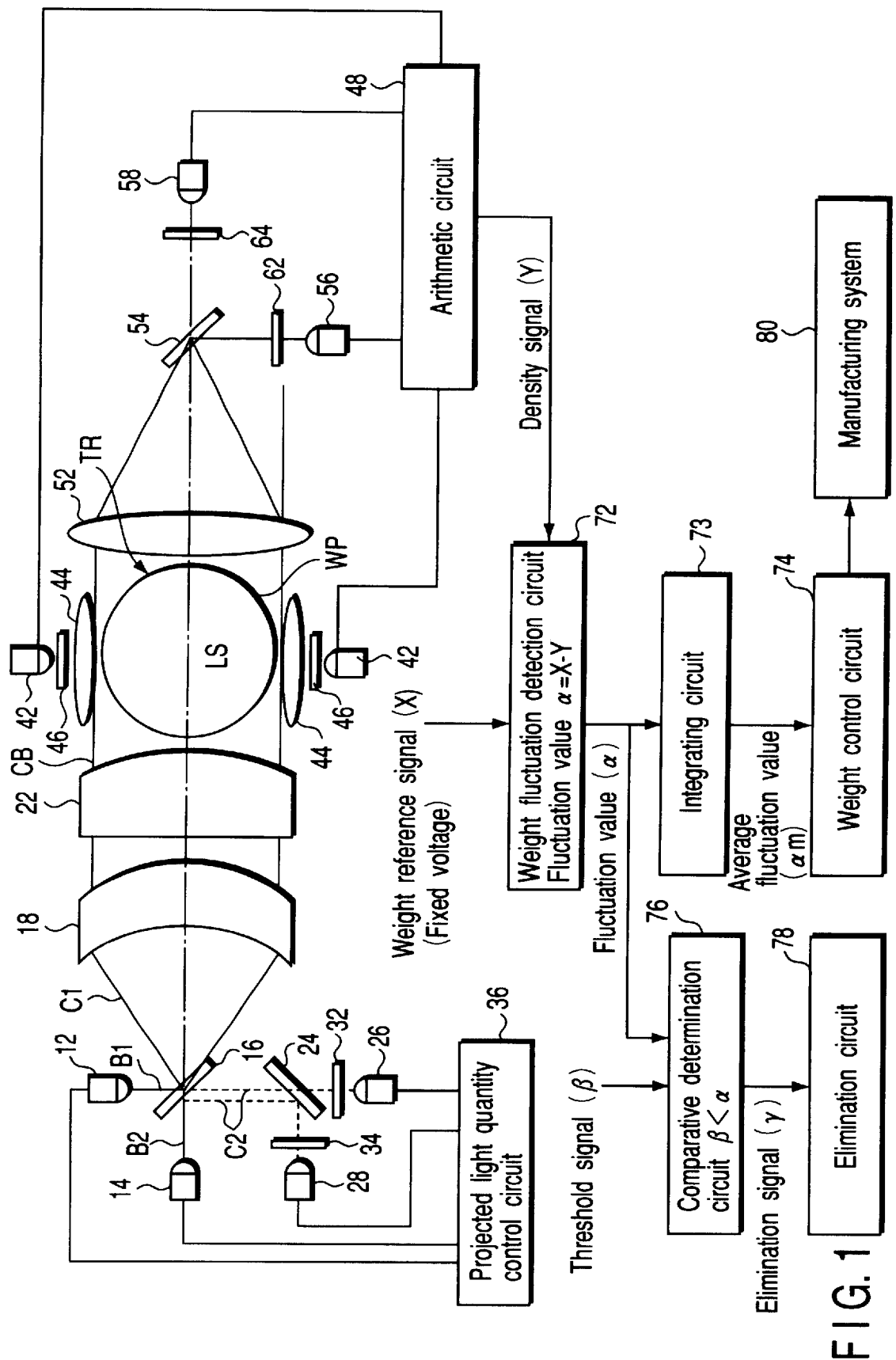
FIG. 1 is a view showing an apparatus for checking the density of shredded leaf tobacco in a tobacco rod according to an embodiment of the present invention.

Embodiments of the present invention will be described with reference to the accompanying drawings. In the following description, constituent elements having substantially the same functions and arrangements are denoted by the same reference numerals, and a repetitive description is made when necessary.

FIG. 1 is a view showing an apparatus for checking the density of shredded leaf tobacco in a tobacco rod according to an embodiment of the present invention.

As shown in FIG. 1, this checking apparatus has first and second light sources 12 and 14 formed of laser diodes for emitting first and second light beams B1 and B2, respectively. The first light beam B1 of the first light source 12 is formed of a laser beam with a single first wavelength of 0.7 $\mu$m. The first wavelength is selected from the range of 0.5 $\mu$m to 0.8 $\mu$m so the first light beam B1 is substantially transmitted through a wrapper WP of a tobacco rod TR serving as a test target but is not substantially transmitted through shredded leaf tobacco LS which is an aggregate of a large number of small pieces. The second light beam B2 of the second light source 14 is formed of a laser beam with a single second wavelength of 1.3 $\mu$m. The second wavelength is selected from the range of 1.2 $\mu$m to 1.4 $\mu$m so the second light beam B2 is substantially transmitted through the wrapper WP and shredded leaf tobacco LS without being substantially influenced by water of the shredded leaf tobacco LS.

The first and second light beams B1 and B2 emitted from the first and second light sources 12 and 14 are synthesized by a half mirror 16. A first synthetic portion C1 synthesized toward the tobacco rod TR as the test target, i.e., the synthetic light beam, is shaped to a parallel light beam CB with a width of about 5 mm (with respect to the diameter of 6 mm to 10 mm of the tobacco rod TR) through a correction lens 18 and collimator lens 22, and is applied to the tobacco rod TR.

A second synthetic portion C2 of the first and second light beams B1 and B2, which is separated from the first synthetic portion C1 by the half mirror 16, is further split by a half mirror 24, and is guided to first and second light-receiving elements 26 and 28. A 0.7-$\mu$m light filter 32 and 1.3-$\mu$m light filter 34 are disposed at the input sides of the first and second light-receiving elements 26 and 28 in order that only light originated from the first and second light beams B1 and B2 become incident on the first and second light-receiving elements 26 and 28.

The received light quantities of the first and second light-receiving elements 26 and 28 are measured by a projected light quantity control circuit 36, so that the first and second projected light quantities of the first and second light beams B1 and B2 included in the parallel light beam CB are monitored. The projected light quantity control circuit 36 calculates the first and second projected light quantities of the first and second light beams B1 and B2 included in the parallel light beam CB, and feedback-controls outputs from the first and second light sources 12 and 14 so that the first and second projected light quantities are constant. The first and second projected light quantities of the first and second light beams B1 and B2 included in the parallel light beam CB are transmitted from the projected light quantity control circuit 36 to an arithmetic circuit 48 (to be described later).

The reflected light of the parallel light beam CB, which is reflected by the surface of the tobacco rod TR, i.e., the surface of the wrapper WP, is focused on a pair of third light-receiving elements 42, disposed above and under the tobacco rod TR, through condenser lenses 44. In this embodiment, since 1.3-$\mu$m light filters 46 are disposed between the third light-receiving elements 42 and condenser lenses 44, only the reflected light of the second light beam B2 become incident on the third light-receiving elements 42.

The received light quantities of the pair of third light-receiving elements 42 are measured by the arithmetic circuit 48. The arithmetic circuit 48 calculates the first and second reflected light quantities of the first and second light beams B1 and B2 included in the parallel light beam CB reflected by the surface of the tobacco rod TR. The received light quantities of the third light-receiving elements 42 are only that of the reflected light of the second light beam B2. However, the arithmetic circuit 48 calculates the first and second reflected light quantities on the premise that the first light beam B1 is also reflected with the same reflectance as that calculated from the reflected light of the second light beam B2. Instead of this arrangement, a light-receiving element for receiving the reflected light of the first light beam B1 may be further disposed in addition to the third light-receiving elements 42 for receiving the reflected light of the second light beam B2.

The transmitted light of the parallel light beam CB, which is transmitted through the tobacco rod TR, is focused on a half mirror 54 by a condenser lens 52 while including light that has detoured along the surface of the tobacco rod TR, and is split by the half mirror 54. The split light beams are guided to fourth and fifth light-receiving elements 56 and 58. A 0.7-$\mu$m light filter 62 and 1.3-$\mu$m light filter 64 are disposed at the input sides of the fourth and fifth light-receiving elements 56 and 58 in order that only light originated from the first and second light beams B1 and B2 become incident on the fourth and fifth light-receiving elements 56 and 58.

The received light quantities of the fourth and fifth light-receiving elements 56 and 58 are also measured by the arithmetic circuit 48. The arithmetic circuit 48 calculates the first and second passing light quantities of the first and second light beams B1 and B2 included in the parallel light beam CB passing through the tobacco rod TR. Since the first light beam B1 with the wavelength of 0.7 $\mu$m is not substantially transmitted through the shredded leaf tobacco LS, light becoming incident on the fourth light-receiving element 56 is the synthesis of light passing through the clearance of the shredded leaf tobacco LS and light detouring along the surface of the tobacco rod TR. Since the second light beam B2 with the wavelength of 1.3 $\mu$m is substantially transmitted through the shredded leaf tobacco LS, light becoming incident on the fifth light-receiving element 58 is the synthesis of light transmitted through the shredded leaf tobacco LS, light passing through the clearance of the shredded leaf tobacco LS, and light detouring along the surface of the tobacco rod TR.

The arithmetic circuit 48 amplifies light reception quantity signals corresponding to the first and second projected light quantities, first and second reflected light quantities, and first and second passing light quantities, and calculates the density of the shredded leaf tobacco LS in the tobacco rod TR on the basis of the signals. This algorithm will be described first with reference to FIGS. 2 and 3 showing simplified models.

Figure 2:
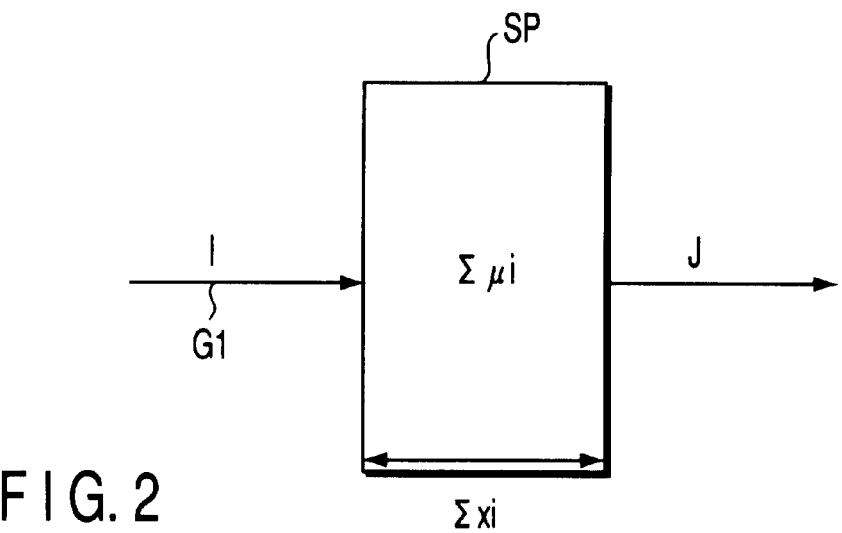
FIG. 2 is a view showing a model wherein a wall-like test target made of an aggregate of a large number of small pieces SP is irradiated with an infrared laser beam G1 to measure the density of the small pieces SP.
Figure 3:
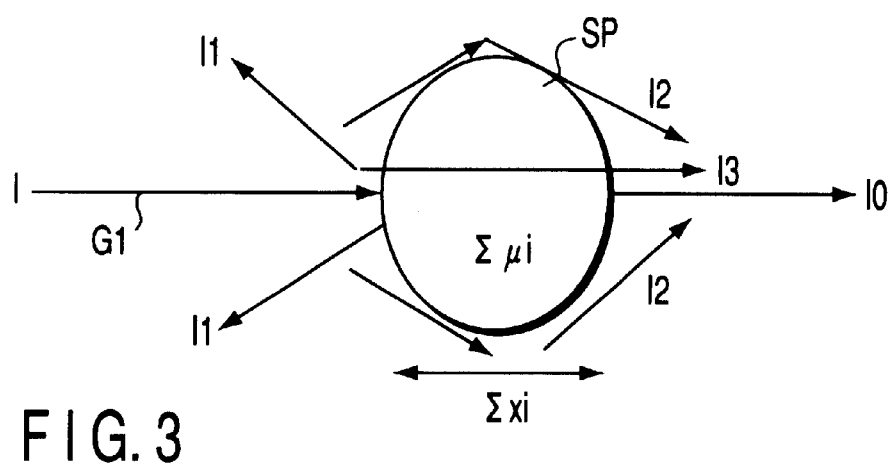
FIG. 3 is a view showing a model wherein a rod-like test target made of an aggregate of a large number of small pieces SP is irradiated with an infrared laser beam G1 to measure the density of the small pieces SP.

FIG. 2 is a view showing a model wherein a wall-like test target made of an aggregate of a large number of small pieces SP is irradiated with an infrared laser beam G1 to measure the density of the small pieces SP. In this case, in an ideal state, the basic relationship between the projected light quantity and transmitted light quantity (passing light quantity=transmitted light quantity in this case) of the laser beam G1 is expressed by the following equation:

$$J = I \cdot \exp(-\Sigma(\mu i \cdot xi))$$

where

I: the projected light quantity of the laser beam G1;

J: the transmitted light quantity of the laser beam G1;

$\mu i$: the transmission coefficient of the small pieces SP; and xi: the thickness of the small pieces SP However, when the density of the shredded leaf tobacco is to be measured by irradiating a rod-like test target such as a tobacco rod with an infrared laser beam, a decrease in incident light quantity caused by light reflected by the surface of the tobacco rod, an increase in passing light quantity caused by light detouring along the surface of the tobacco rod, and noise included in the passing light quantity caused by light passing through the shredded leaf tobacco must be considered. FIG. 3 is a view showing a model wherein a rod-like test target made of an aggregate of a large number of small pieces SP is irradiated with an infrared laser beam G1 to measure the density of the small pieces SP. In the model shown in FIG. 3, when the above factors are considered, the relationship between the projected light quantity and passing light quantity of the laser beam G1 is expressed by the following equation:

$$I_0-I_2-I_3=(I-I_1)\cdot\exp(-\Sigma(\mu i\cdot xi)) \tag{1}$$

where

I: the projected light quantity of the laser beam G1;

$I_0$: the passing light quantity of the laser beam G1;

$I_1$: the reflected light quantity of the laser beam G1;

$I_2$: the detouring light quantity of the laser beam G1;

$I_3$: the quantity of light passing through the small pieces SP of the laser beam G1;

$\mu i$: the transmission coefficient of the small pieces SP; and $xi$: the thickness of the small pieces SP In the case of the tobacco rod TR, the transmission coefficient $\mu i$ of each piece of the shredded leaf tobacco LS can be known in advance. A total thickness $\Sigma xi$ of the shredded leaf tobacco LS is closely related to the packing density of the shredded leaf tobacco, and the transmission coefficient $\mu i$ of the shredded leaf tobacco is substantially constant. Therefore, even in the apparatus shown in FIG. 1, if values corresponding to I, $I_0$, $I_1$, $I_2$, and $I_3$ in equation (1) are measured, the total thickness of the shredded leaf tobacco LS in the transmission path of the parallel light beam CB can be obtained. Once the total thickness is obtained, the packing density of the shredded leaf tobacco LS can be calculated at high precision by multiplying it by a predetermined coefficient.

In the apparatus shown in FIG. 1, what corresponds to the laser beam G1 of the model shown in FIG. 3 is the second light beam B2 included in the parallel light beam CB emerging from the collimator lens 22. More specifically, I of equation (1) corresponds to the projected light quantity (calculated by the projected light quantity control circuit 36) of the second light beam B2 included in the parallel light beam CB emerging from the collimator lens 22. $I_1$ of equation (1) corresponds to the reflected light quantity (received by the third light-receiving elements 42) of the second light beam B2 included in the parallel light beam CB reflected by the surface of the tobacco rod TR. $I_0$ of equation (1) corresponds to the passing light quantity (received by the fifth light-receiving element 58) of the second light beam B2 included in the parallel light beam CB passing through the tobacco rod TR.

$I_2$ and $I_3$ of equation (1) each correspond to part of the passing light quantity of the second light beam B2 included in the parallel light beam CB passing through the tobacco rod TR. Hence, $I_2$ and $I_3$ cannot be directly measured in the apparatus shown in FIG. 1. In the present invention, however, the total noise light quantity $I_2+I_3$ of light detouring along the surface of the tobacco rod and light passing through the shredded leaf tobacco, which concern the second light beam B2, can be estimated from the net projected light quantity and passing light quantity of the first light beam B1.

More specifically, the arithmetic circuit 48 calculates the net projected light quantities of the first and second light beams B1 and B2. The net projected light quantities can be obtained by subtracting the reflected light quantities of the first and second light beams B1 and B2 included in the parallel light beam CB reflected by the surface of the tobacco rod TR, from the projected light quantities of the first and second light beams B1 and B2 included in the parallel light beam CB emerging from the collimator lens 22. The projected light quantities of the first and second light beams B1 and B2 are calculated by the projected light quantity control circuit 36 on the basis of light received by the first and second light-receiving elements 26 and 28. The reflected light quantities of the first and second light beams B1 and B2 are calculated by the arithmetic circuit 48 on the basis of light received by the third light-receiving elements 42.

Subsequently, the ratios (attenuation ratios) of the passing light quantities of the first light beams B1 and B2 to the net projected light quantities are calculated. The passing light quantities of the first light beams B1 and B2 are calculated by the arithmetic circuit 48 on the basis of light received by the fourth and fifth light-receiving elements 56 and 58. As described above, since the first light beam B1 with the wavelength of 0.7 $\mu$m is not substantially transmitted through the shredded leaf tobacco LS, light becoming incident on the fourth light-receiving element 56 is the synthesis of light passing through the clearance of the shredded leaf tobacco LS and light detouring along the surface of the tobacco rod TR. Since the second light beam B1 with the wavelength of 1.3 $\mu$m is substantially transmitted through the shredded leaf tobacco LS, light becoming incident on the fifth light-receiving element 58 is the synthesis of light transmitted through the shredded leaf tobacco LS, light passing through the clearance of the shredded leaf tobacco LS, and light detouring along the surface of the tobacco rod TR.

Subsequently, the total noise light quantity of the light detouring along the surface of the tobacco rod and the light passing through the shredded leaf tobacco, which concern the second light beam B2, is estimated from the net projected light quantity and passing light quantity of the first light beam B1. The total noise light quantity is subtracted from the passing light quantity of the second light beam B2, thereby obtaining the transmitted light quantity of the second light beam B2 transmitted through the shredded leaf tobacco LS.

For example, assume that the attenuation ratio, i.e., (passing light quantity)/(net projected light quantity), of the first light beam B1 is 10%, and that the attenuation ratio, i.e., (passing light quantity)/(net projected light quantity), of the second light beam B2 is 30%. In this case, it is estimated that, of the attenuation ratio 30% of the second light beam B2, 10% is originated from the light detouring along the surface of the tobacco rod and the light passing through the shredded leaf tobacco, and 20% is originated from the light transmitted through the shredded leaf tobacco LS. In other words, the net light quantity, i.e., the transmitted light quantity, corresponding to $I_0-I_2-I_3$ of equation (1) can be obtained by subtracting the attenuation ratio of the first light beam B1 from that of the second light beam B2.

The arithmetic circuit 48 calculates $\Sigma xi$ from the net projected light quantity $(I-I_1)$ and transmitted light quantity $(I_0-I_2-I_3)$ calculated in this manner and the transmission coefficient $\mu i$ of the shredded leaf tobacco LS input in advance, and multiplies it by a predetermined coefficient, thus calculating the density of the shredded leaf tobacco LS in the tobacco rod TR. The arithmetic circuit 48 includes an integrating circuit for integrating the signal for a time of 100 $\mu$S to 1 mS, so the adverse influence of noise that can be generated momentarily in the detection signal is removed.

A density signal Y calculated by the arithmetic circuit 48 and representing the density of the shredded leaf tobacco LS is transmitted to a weight fluctuation detection circuit 72. The weight fluctuation detection circuit 72 calculates as a fluctuation value $\alpha$ a difference (X–Y) between a weight reference signal X as the reference value of the density of the shredded leaf tobacco LS and the density signal Y calculated by the arithmetic circuit 48. The weight reference signal X is a voltage corresponding to the transmission amount of light which attenuates when standard packing determined in accordance with the type of tobacco is performed.

The fluctuation value $\alpha$ calculated by the weight fluctuation detection circuit 72 is transmitted to an integrating circuit 73. The integrating circuit 73 calculates an average fluctuation value $\alpha m$ of several hundred tobacco rods TR by integrating the fluctuation values $\alpha$ for a long period of time. The average fluctuation value $\alpha m$ calculated by the integrating circuit 73 is transmitted to a weight control circuit 74 added to a manufacturing system 80 for the tobacco rod TR. The weight control circuit 74 controls the amount of shredded leaf tobacco LS to be packed in each tobacco rod TR in the manufacturing system 80 for the tobacco rod TR on the basis of the average fluctuation value αm.

The fluctuation value α calculated by the weight fluctuation detection circuit 72 is also transferred to a comparative determination circuit 76. The comparative determination circuit 76 compares a preset threshold signal β as the threshold of the fluctuation value α with the fluctuation value α calculated by the weight fluctuation detection circuit 72, and determines whether the tobacco rod TR is defective or not. If it is determined that the tobacco rod TR is defective (β<α), an elimination signal γ is transmitted from the comparative determination circuit 76 to an elimination circuit 78. The elimination circuit 78 eliminates the tobacco rod TR determined defective from the manufacture line on the basis of the elimination signal γ.

Figure 5:
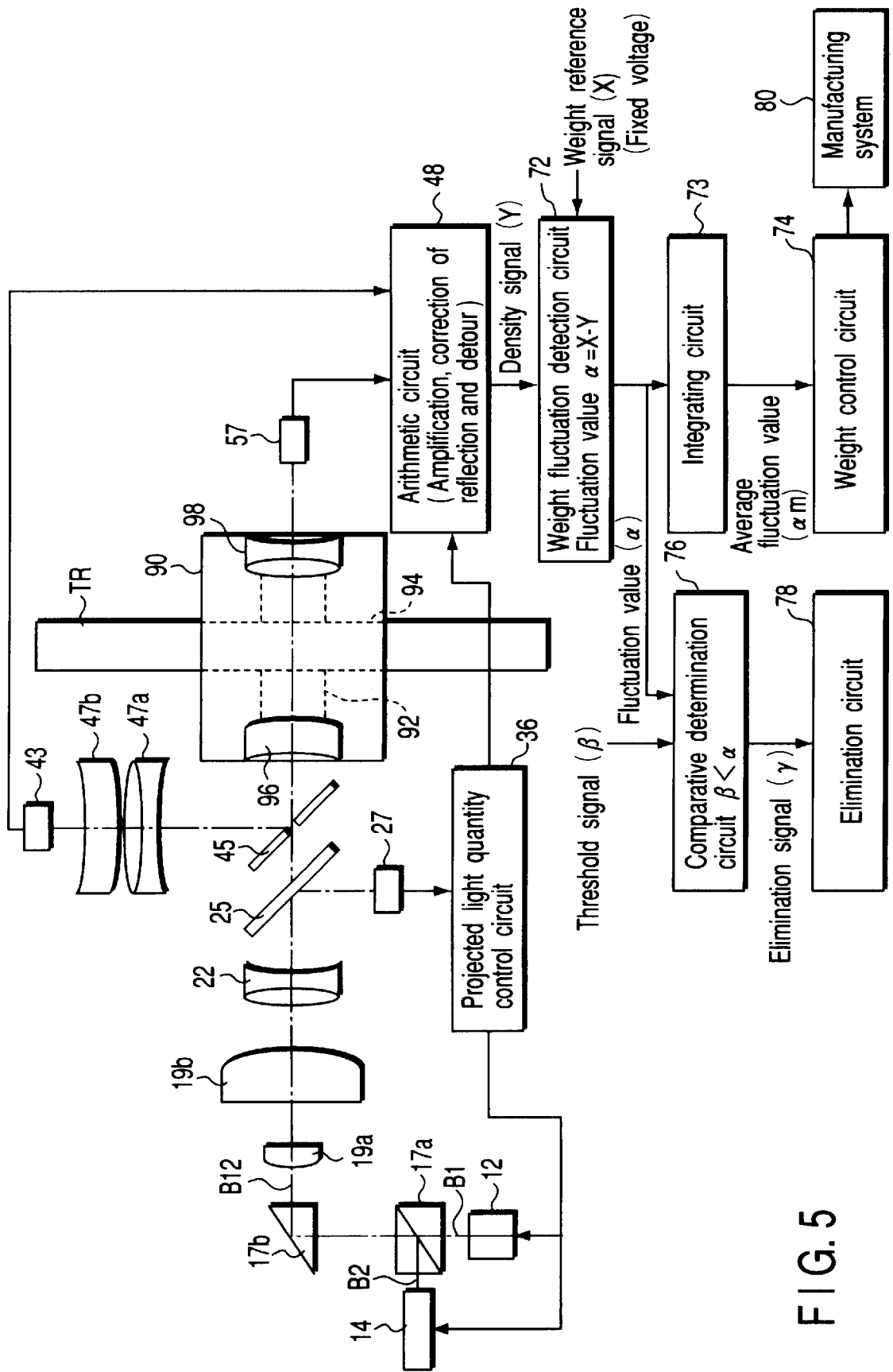
FIG. 5 is a view showing an apparatus for checking the density of shredded leaf tobacco in a tobacco rod according to another embodiment of the present invention.

FIG. 5 is a view showing an apparatus for checking the density of shredded leaf tobacco in a tobacco rod according to another embodiment of the present invention. The basic concept of this embodiment is the same as that of the embodiment shown in FIG. 1. Hence, a description of the second embodiment will be made mainly on the difference from the embodiment shown in FIG. 1.

As shown in FIG. 5, this checking apparatus has a mounting block 90 for mounting a tobacco rod TR as a test target therein. The mounting block 90 is formed of a metal solid body with cylindrical holes 92 and 94 in two directions perpendicular to each other. One hole 92 is formed coaxially with the optical axis of a parallel light beam CB (synthesis light beam) for check. The inner surface of the hole 92 is mirror-finished in order to prevent light absorption. A cylinder lens 96 and collimator lens 98 are disposed at the input and output sides, respectively, of the hole 92. The other hole 94 is formed as a hole where the tobacco rod TR is to be inserted. The diameter of the hole 94 is selected such that no clearance is substantially formed when the tobacco rod TR is inserted in the hole 94.

This checking apparatus also has first and second light sources 12 and 14 formed of laser diodes for respectively emitting first and second light beams B1 and B2. The wavelengths of the first and second light beams B1 and B2 are selected to satisfy the conditions described with reference to the apparatus shown in FIG. 1. More specifically, the wavelengths of the first and second light beams B1 and B2 are set at, e.g., 0.7 μm and 1.3 μm, respectively, as described above.

The first and second light beams B1 and B2 from the first and second light sources 12 and 14 are synthesized by a half mirror prism 17a to form a synthetic light beam B12. The synthetic light beam B12 is switched by a prism 17b toward the mounting block 90, and is shaped to a convergent light beam through cylinder lenses 19a and 19b and a collimator lens 22. The focal point of the convergent light beam is set to fall on a center hole 45a of a mirror 45 disposed immediately before the mounting block 90. The mirror 45 is arranged such that its mirror surface is inclined with respect to the mounting block 90 so as to face it at an angle of, e.g., 45°, and that its center hole 45a is coaxial with the optical axis.

A beam splitter 25 is disposed between the collimator lens 22 and mirror 45, and splits the synthetic light beam B12. A beam portion separated from the check beam portion of the synthetic light beam B12 by the beam splitter 25 is guided to a composite light-receiving element 27. The composite light-receiving element 27 is an element for receiving and detecting two light beams with different wavelengths on one optical path, and in this case is set to match the wavelengths of the first and second light beams B1 and B2. The composite light-receiving element will be described later in detail.

The received light quantity of the composite light-receiving element 27 is measured by a projected light quantity control circuit 36, so the first and second projected light quantities of the first and second light beams B1 and B2 included in the synthetic light beam B12 are monitored. The projected light quantity control circuit 36 calculates the first and second projected light quantities, feedback-controls outputs from the first and second light sources 12 and 14, and transmits the first and second projected light quantities to an arithmetic circuit 48.

The check beam portion of the synthetic light beam B12 passes through the center hole 45a of the mirror 45, is shaped to a parallel light beam by the cylinder lens 96 at the input side of the mounting block 90, and is applied to the tobacco rod TR. The light reflected by the surface of the tobacco rod TR is reflected by the mirror 45 and is guided to a composite light-receiving element 43 through aspherical condenser lenses 47a and 47b. The composite light-receiving element 43 can also receive and detect the first and second light beams B1 and B2 of the reflected light on one optical path. The received light quantity of the composite light-receiving element 43 is measured by the arithmetic circuit 48, so the first and second reflected light quantities of the first and second light beams B1 and B2 are monitored.

The check beam portion passing through the tobacco rod TR is shaped to a converging light beam by the collimator lens 98 at the output side of the mounting block 90, and is guided to a composite light-receiving element 57. The composite light-receiving element 57 can also receive and detect the first and second light beams B1 and B2 of the passing light on one optical path. The received light quantity of the composite light-receiving element 57 is measured by the arithmetic circuit 48, so the first and second passing light quantities of the first and second light beams B1 and B2 are monitored.

The arithmetic circuit 48 calculates the density of shredded leaf tobacco LS in the tobacco rod TR by using the first and second projected light quantities, first and second reflected light quantities, and first and second passing light quantities of the first and second light beams B1 and B2 which are obtained in this manner. Control operation from a weight fluctuation detection circuit 72 to an elimination circuit 78 or manufacturing system 80 is completely the same as that described with reference to the apparatus shown in FIG. 1.

In this embodiment, the algorithm used for calculation of the density of the shredded leaf tobacco LS is basically the same as that described with reference to the embodiment shown in FIG. 1. Note that in the embodiment shown in FIG. 1, the first reflected light quantity of the first light beam B1 is calculated on the basis of the second reflected light quantity of the second light beam B2, whereas in the second embodiment, it is measured by actually receiving and detecting the first reflected light quantity of the first light beam B1. Accordingly, in this embodiment, if the test target has different reflectances depending on the wavelengths, no error is caused.

Figure 4:
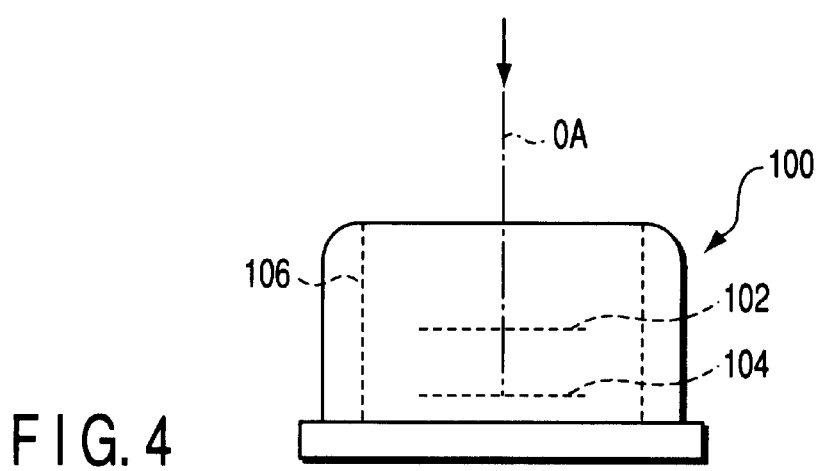
FIG. 4 is a side view showing a composite light-receiving element that receives and detects two light beams with different wavelengths on one optical path.

FIG. 4 is a side view showing a composite light-receiving element 100 used as each of the composite light-receiving elements 27, 43, and 57. As shown in FIG. 4, the composite light-receiving element 100 has light-receiving portions 102 and 104 disposed at two different levels perpendicular to an optical axis OA of an incident light beam. The light-receiving portions 102 and 104 are formed of different semiconductor light-receiving elements. The primary (upper) light-receiving portion 102 detects the first light beam B1 with a short wavelength (0.7 μm in this case), and the secondary (lower) light-receiving portion 104 detects the second light beam B2 with a long wavelength (1.3 μm in this case) which can pass through the primary light-receiving portion 102. A Peltier element 106 for cooling the light-receiving portions 102 and 104 is disposed on the inner surface of the housing of the composite light-receiving element 100.

In this manner, when a composite light-receiving element that can receive and detect the first and second light beams B1 and B2 on one optical path is used, a great advantage can be obtained in terms of cost and space. Concerning this point, each of the first and second light beams B1 and B2 from the first and second light sources 12 and 14 is a laser light beam and accordingly has a single wavelength. Therefore, even if processing such as wavelength separation is not performed before the light is received, the composite light-receiving element will not detect light in which the wavelengths of the first and second light beams B1 and B2 are mixed. When the light-receiving portions 102 and 104 are cooled by the Peltier element 106, temperature drift or noise caused by overheat of the light-receiving portions 102 and 104 can be prevented.

The preferred embodiments of the present invention have been described with reference to the accompanying drawings. Note that the present invention is not limited to the above arrangements. Various types of modifications and changes within the scope of the technical concept described in the claims may be anticipated by a person skilled in the art. It is to be understood that these modifications and changes belong to the technical range of the present invention.

Additional advantages and modifications will readily occur to those skilled in the art. Therefore, the invention in its broader aspects is not limited to the specific details and representative embodiments shown and described herein. Accordingly, various modifications may be made without departing from the spirit or scope of the general inventive concept as defined by the appended claims and their equivalents.

What is claimed is:

1. An apparatus directed to as a test target a rod-like flavor-tasting article or a component thereof having an aggregate of a large number of small pieces, to optically check the density of the small pieces, comprising:

a first light source configured to emit a first light beam formed of light with a first wavelength not substantially transmitted through the small pieces;

a second light source configured to emit a second light beam formed of light with a second wavelength substantially transmitted through the small piece;

an optical system configured to synthesize the first and second light beams and to irradiate the test target with an obtained synthetic light beam;

a first measurement unit configured to measure first and second projected light quantities respectively corresponding to the first and second light beams included in the synthetic light beam before applied to the test target;

a second measurement unit configured to measure first and second reflected light quantities respectively corresponding to the first and second light beams included in the synthetic light beam reflected by a surface of the test target;

a third measurement unit configured to measure first and second passing light quantities respectively corresponding to the first and second light beams included in the synthetic light beam passing through the test target; and an arithmetic circuit configured to calculate a transmitted light quantity of the second light beam transmitted through the small pieces on the basis of the first and second projected light quantities, first and second reflected light quantities, and first and second passing light quantities, and to calculate the density of the small pieces on the basis of the transmitted light quantity.

2. The apparatus according to claim 1, wherein the second measurement unit measures the first and second reflected light quantities by receiving and detecting both the first and second light beams included in the synthetic light beam reflected by the surface of the test target.

3. The apparatus according to claim 1, wherein the second measurement unit measures one of the first and second reflected light quantities by receiving and detecting one of the first and second light beams included in the synthetic light beam reflected by the surface of the test target, and measures the other one of the first and second reflected light quantities by calculation with a premise that the other one of the first and second reflected light quantities can be obtained with the same reflectance as that of one of the reflected light quantities.

4. The apparatus according to claim 1, further comprising a detection circuit configured to calculate a fluctuation value as a difference between a reference value representing the density of the small pieces and a measurement value of the density of the small pieces which is obtained by the arithmetic circuit, and a control circuit configured to control an amount of the small pieces to be introduced into the test target in a manufacturing system for the test target on the basis of the fluctuation value.

5. The apparatus according to claim 4, further comprising an integrating circuit configured to calculate an average value of fluctuation values of a plurality of test targets obtained with the detection circuit and to transmit the average value to the control circuit.

6. The apparatus according to claim 4, further comprising a comparative determination circuit configured to compare the fluctuation value and a threshold value and to determine whether the test target is defective or not.

7. The apparatus according to claim 1, wherein the small pieces are shredded leaf tobacco, and the first and second wavelengths are 0.5 $\mu$m to 0.8 $\mu$m and 1.2 $\mu$m to 1.4 $\mu$m, respectively.

8. The apparatus according to claim 1, wherein each of the first and second light beams comprises a laser light beam.

9. The apparatus according to claim 8, wherein at least one of the first to third measurement units has a composite light-receiving element configured to receive and detect the first and second light beams on one optical path.

10. The apparatus according to claim 1, wherein the synthetic light beam applied from the optical system to the test target comprises a parallel light beam.

11. The apparatus according to claim 1, wherein the first measurement unit measures the first and second projected light quantities by receiving and detecting the first and second light beams included in a beam portion separated from the synthetic light beam between the optical system and the test target.

12. The apparatus according to claim 1, further comprising a mirror, which is disposed between the optical system and the test target, and has a mirror surface facing the test target to be inclined with respect thereto and a hole matching with an optical axis of the optical system, wherein the synthetic light beam from the optical system passes through the hole as a convergent light beam with a focal point falling on the hole and is thereafter applied to the test target, and the synthetic light beam reflected by the surface of the test target is reflected by the mirror and is introduced to the second measurement unit.

* * * * *